United States Patent
Arumugam et al.

(10) Patent No.: US 10,071,956 B2
(45) Date of Patent: Sep. 11, 2018

(54) PROCESS FOR THE PREPARATION OF DIBENZENESULFONIMIDE

(71) Applicant: SRF Limited, Haryana (IN)

(72) Inventors: Thirupathi Arumugam, Haryana (IN); Mariano Patrick Philips, Haryana (IN); Dilli Babu, Haryana (IN); Maheshwaran Chellaiah, Haryana (IN); Sarathy Iyengar, Haryana (IN); Rajdeep Anand, Haryana (IN)

(73) Assignee: SRF LIMITED (IN)

( * ) Notice: Subject to any disclaimer, the term of this patent is extended or adjusted under 35 U.S.C. 154(b) by 0 days.

(21) Appl. No.: 15/326,379

(22) PCT Filed: Jul. 15, 2015

(86) PCT No.: PCT/IN2015/000283
§ 371 (c)(1),
(2) Date: Jan. 13, 2017

(87) PCT Pub. No.: WO2016/009448
PCT Pub. Date: Jan. 21, 2016

(65) Prior Publication Data
US 2017/0210705 A1    Jul. 27, 2017

(30) Foreign Application Priority Data
Jul. 15, 2014  (IN) .......................... 1990/DEL/2014

(51) Int. Cl.
*C07C 303/38* (2006.01)
*C07C 311/48* (2006.01)
(52) U.S. Cl.
CPC .......... *C07C 303/38* (2013.01); *C07C 311/48* (2013.01)

(58) Field of Classification Search
None
See application file for complete search history.

(56) References Cited

FOREIGN PATENT DOCUMENTS

CN      101671285    *    3/2010

OTHER PUBLICATIONS

Wang ("Enantioselective Fluorination of 2-Oxindoles by Structure-Micro-Tuned N-Fluorobenzenesulfonamides" European Journal of Organic Chemistry, Apr. 24, 2014, p. 3607-3613).*
Dong ("Copper-Catalyzed Trifluoromethylation and Cyclization of Aromatic-Sulfonyl-Group-Tethered Alkenes for the Construction of 1,2-Benzothiazinane Dioxide Type Compounds" Chemistry, a European Journal, 2013, 19, p. 16910-16915, including Supporting Information p. S1-S80) (Year: 2013).*
Dichloromethane (DCM) (Sigma Aldrich Dichloromethane Physical Property Sheet, p. 1-2, downloaded from https://www.sigmaaldrich.com/chemistry/solvents/dichloromethane-center.html on Nov. 5, 2017) (Year: 2017).*
Mei ("Bis(diaryliodonium)perfluorosulfonimide zwitterions as potential photo acid generators" Journal of Fluorine Chemistry, 160, Jan. 17, 2014, p. 12-15) (Year: 2014).*
International Search Report and Written Opinion of PCT/IN2015/000283, dated Nov. 17, 2015, 12 pages.

* cited by examiner

*Primary Examiner* — Jafar Parsa
*Assistant Examiner* — Amy C Bonaparte
(74) *Attorney, Agent, or Firm* — Blank Rome LLP

(57) ABSTRACT

The present invention provides a process for the preparation of dibenzenesulfonimide.

2 Claims, No Drawings

PROCESS FOR THE PREPARATION OF DIBENZENESULFONIMIDE

RELATED APPLICATIONS

This application is a national phase of PCT/IN2015/000283, filed on Jul. 15, 2015, which claims the benefit of Indian Patent Application No. 1990/DEL/2014, filed on Jul. 15, 2014. The content of these applications are hereby incorporated by reference.

FIELD OF THE INVENTION

The present invention provides a process for the preparation of dibenzenesulfonimide of Formula I.

BACKGROUND OF THE INVENTION

The dibenzenesulfonimide of Formula I is a useful intermediate for the preparation of corresponding N-fluorosulfonimide of Formula II. The use of N-fluorosulfonimide for fluorination of nucleophilic organic compounds is well known. Further, these fluorine substituents play an important role in preparation of pharmaceutical and agrochemical agents.

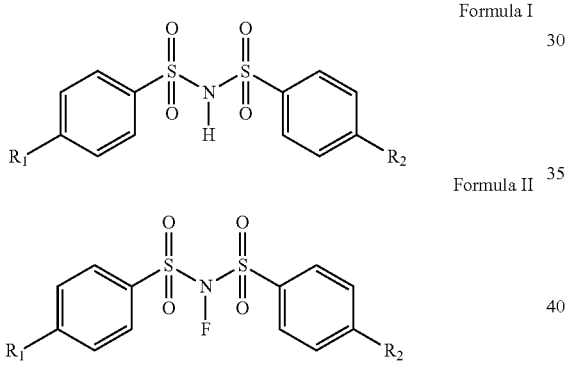

Formula I

Formula II where $R_1$ and $R_2$ are independently selected from group consisting of fluorine, chlorine, bromine, iodine, $C_{1-6}$ alkyl, $C_{1-6}$alkoxy, $C_{1-6}$alkylsulfonyl, $C_{1-6}$perfluoroalkylsulfonyl and cyano.

The process for the preparation of substituted and un-substituted benzenesulfonimides has been studied widely, for example, U.S. Pat. Nos. 2,891,979 and 5,254,732. Most recently the CN patent application 101671285 provides a process for preparation of dibenzenesulfonimide by reacting benzenesulfonamide with benzene sulfonyl chloride in the presence of sodium hydroxide and water.

The present inventors have observed that use of inorganic strong bases and water, such as alkali hydroxides and water, while condensation of benzenesulfonamide with benzene sulfonyl chloride results in great yield loss. This is primarily because benzene sulfonyl chloride gets hydrolysed to corresponding acid in the presence of inorganic strong bases and water, thus resulting in yield loss. Further, the inventors of the present invention found that the condensation of benzenesulfonamide with benzene sulfonyl chloride in the presence of compound of Formula V results in unexpected increase of reaction yield and simultaneously avoids any side reactions.

OBJECT OF THE INVENTION

It is an object of the present invention to provide a process for the preparation of dibenzenesulfonimide of Formula I:

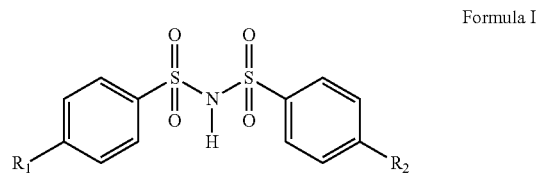

Formula I

SUMMARY OF THE INVENTION

The present invention provides a process for the preparation of dibenzenesulfonimide of Formula I,

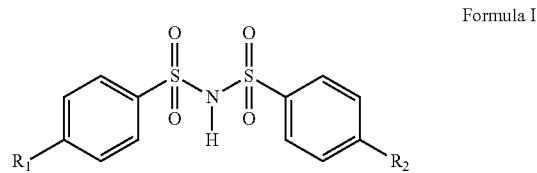

Formula I the process comprising;
a) treating compound of Formula III with compound of Formula IV in the presence of compound of Formula V,

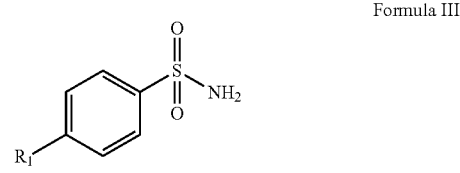

Formula III

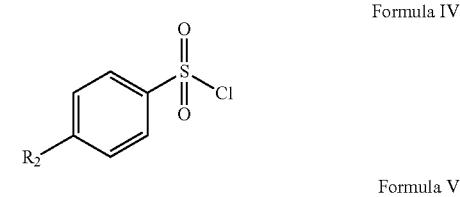

Formula IV

Formula V where $R_1$ and $R_2$ are independently selected from group consisting of fluorine, chlorine, bromine, iodine, $C_{1-6}$ alkyl, $C_{1-6}$alkoxy, $C_{1-6}$alkylsulfonyl, $C_{1-6}$perfluoroalkylsulfonyl and cyano,
the $R_3$, $R_4$ and $R_5$ are independently selected from optionally substituted $C_{1-6}$alkyl and optionally substituted $C_{1-6}$ aryl,
b) isolating the compound of Formula I from the reaction mixture.

DETAILED DESCRIPTION OF THE INVENTION

In an aspect, the present invention provides a process for the preparation of dibenzenesulfonimide of Formula I,

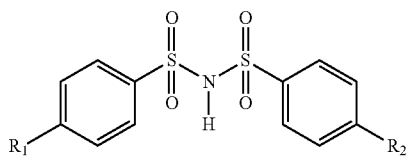

Formula I the process comprising;
a) treating compound of Formula III with compound of Formula IV in the presence of compound of Formula V,

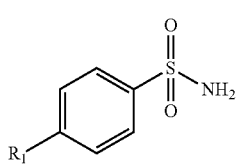

Formula III

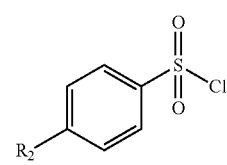

Formula IV

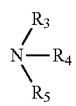

Formula V where $R_1$ and $R_2$ are independently selected from group consisting of fluorine, chlorine, bromine, iodine, $C_{1-6}$ alkyl, $C_{1-6}$ alkoxy, $C_{1-6}$alkylsulfonyl, $C_{1-6}$perfluoroalkylsulfonyl and cyano,
the $R_3$, $R_4$ and $R_5$ are independently selected from optionally substituted $C_{1-6}$ alkyl and optionally substituted $C_{1-6}$ aryl,
b) isolating the compound of Formula I from the reaction mixture.

The compounds of Formula III and Formula IV are obtainable by known processes or commercially available. The condensation of compound of Formula III and compound of Formula IV takes place in the presence of compound of Formula V. The condensation of compound of Formula III and compound of Formula IV may take place at a temperature of about 0° C. to about 100° C., for example, about 10° C. to about 40° C. for about 10 minutes to about 10 hours, for example, for about 2 hours to about 5 hours. The condensation of compound of Formula III and compound of Formula IV may take place in the presence of solvent, for example, acetonitrile. The condensation may be facilitated by stirring the reaction mixture. The reaction completion is monitored by High Performance Liquid Chromatography.

The compound of Formula I is isolated from the reaction mixture by layer separation, distillation, filtration, evaporation and decantation or mixture thereof. The compound of Formula I, obtained by present invention, has the purity greater than about 98%, preferably greater than 98.5%, more preferably greater than 99% by High Performance Liquid Chromatography.

While the present invention has been described in terms of its specific embodiments, certain modifications and equivalents will be apparent to those skilled in the art and are intended to be included within the scope of the present invention.

EXAMPLE

Example 1

Preparation of Dibenzenesulfonimide

Benzenesulfonamide (50 g), acetonitrile (150 g) and triethylamine (97 g) were taken in a reaction vessel and stirred for 45 minutes. The benzene sulfonyl chloride (69 g) was added drop-wise to the reaction mixture at 20° C. The reaction mixture was additionally stirred at 25° C. for 45 minutes. The acetonitrile was recovered by evaporation and solid reaction mass was dissolved in sodium hydroxide (20%, 300 g). The aqueous layer was separated, washed with chloroform and acidified with hydrochloric acid (35%) to obtain the title product.

Yield (g): 90
Purity (% by HPLC): 99.2

We claim:
1. A process for preparing a dibenzenesulfonimide of Formula I,

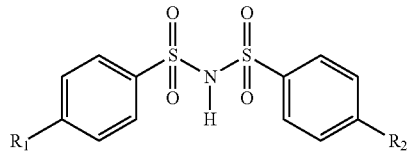

Formula I comprising the steps of:
a) treating a compound of Formula III with a compound of Formula IV in the presence of a compound of Formula V in acetonitrile at a temperature of below 30° C.,

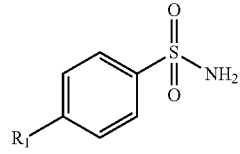

Formula III

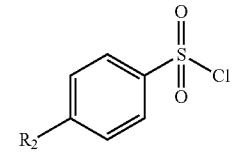

Formula IV

Formula V wherein $R_1$ and $R_2$ are independently selected from the group consisting of hydrogen, fluorine, chlorine, bromine, iodine, $C_{1-6}$ alkyl, $C_{1-6}$ alkoxy, $C_{1-6}$ alkylsulfonyl, $C_{1-6}$ perfluoroalkylsulfonyl and cyano; and $R_3$, $R_4$ and $R_5$ are independently selected from the group consisting of optionally substituted $C_{1-6}$ alkyl and optionally substituted $C_{1-6}$ aryl, and b) isolating the compound of Formula I.

2. The process of claim 1, wherein step b) is carried out by layer separation, distillation, filtration, evaporation, decantation, or a combination thereof.

* * * * *